United States Patent [19]

Kurahashi et al.

[11] Patent Number: 4,522,204
[45] Date of Patent: Jun. 11, 1985

[54] RESPIRATORY GAS CONCENTRATION MEASURING APPARATUS

[75] Inventors: Muneshige Kurahashi, Saitama; Shinji Yamamori, Tokyo, both of Japan

[73] Assignee: Nihon Kohden Corporation, Tokyo, Japan

[21] Appl. No.: 502,133

[22] Filed: Jun. 8, 1983

[30] Foreign Application Priority Data

Jun. 22, 1982 [JP] Japan ................. 57-106174

[51] Int. Cl.$^3$ .............................................. A61B 5/00
[52] U.S. Cl. ................................... 128/719; 356/418; 250/343
[58] Field of Search ............. 128/665, 666, 719; 73/23; 250/214 C, 565, 343; 356/39–42, 418, 419

[56] References Cited

U.S. PATENT DOCUMENTS 3,724,954  4/1973  Dreyfoos, Jr. ..................... 356/418
4,067,320  1/1978  Olsson et al. ..................... 128/719
4,312,593  1/1982  Baker et al. ....................... 356/418

Primary Examiner—Kyle L. Howell
Assistant Examiner—Ruth Smith
Attorney, Agent, or Firm—Hoffmann, Dilworth, Barrese & Baron

[57] ABSTRACT

A respiratory gas concentration measuring apparatus includes a chopper having a first filter for passing therethrough light from a light source and having a first wavelength which can be absorbed by a gas to be measured and a second filter for passing therethrough light from the light source and having a second wavelength which cannot be absorbed by the gas. The chopper is rotatable to position the first and second filters alternately in a light path. The light having passed through the filters is converted by a photodetector into an electric signal. A first detector detects an output from the first filter based on the electric signal, and a second detector detects an output from the second filter based on the electric signal. The apparatus has a power computing circuit for raising an output from said second detector to an mth power, m being a power exponent preset in the power computing circuit, and a divider circuit for dividing an output from the first detector by an output from the power computing circuit. The power exponent m is the ratio between a temperature-dependent coefficient $\theta_1$ of the output of the first detector which varies exponentially with a temperature variation and a temperature-dependent coefficient $\theta_2$ of the output of the second detector which varies exponentially with a temperature variation.

1 Claim, 2 Drawing Figures

RESPIRATORY GAS CONCENTRATION MEASURING APPARATUS

BACKGROUND OF THE INVENTION

The present invention relates to a respiratory gas concentration measuring apparatus for measuring the concentrations of $CO_2$, $N_2O$, anesthesia gas or other gases in respiratory gas based on the absorption of gases to be measured with respect to light of a particular wavelength which passes therethrough.

One known type of respiratory gas concentration measuring apparatus is shown in Japanese Laid-Open Patent Publication No. Sho 57-23843. According to the disclosed apparatus, which is illustrated in FIG. 1 of the accompanying drawings, a respiratory gas concentration is measured on the basis of the Lambert-Beer's law:

$$V_s = V_o e^{-KC} \qquad (1)$$

where Vs: photoelectric conversion output, Vo: Vs at the time of zero gas concentration, K: proportionality constant, and C: gas concentration.

The prior apparatus as shown includes a connector tube 2 having a tube end 210 to be held in the mouth of an examinee 1, an opposite open end 220 to be vent to atmosphere or connected to an artificial respiratory system, an anesthetizer or the like, and a pair of intermediate windows 3 opening at central portions of the connector tube 2 in confronting relation and rendered airtight by transparent sapphire or the like. The apparatus also has a light source 4, a power supply 5, and a rotatable chopper 6.

The chopper 6 has a pair of filters 7, 8 disposed in diametrically opposite relation. The filter 7 is capable of passing therethrough only light having a wavelength that can be absorbed by $CO_2$ gas. The filter 8 allows passage therethrough of light having a wavelength that cannot be absorbed by $CO_2$ gas. The chopper 6 is rotated at a constant cyclic period by a motor 9. A photodetector 10 serves to convert an amount of light falling thereon into a corresponding electric signal, which is fed to an amplifier 11. An output from the amplifier 11 is supplied to a pair of first and second detectors 12, 13. The first detector 12 serves to detect a signal in synchronism with positional alignment of the filter 7 with a path of light (shown by the dotted lines in FIG. 1) passing through the windows 3. The second detector 13 can detect a signal in synchronism with positional alignment of the filter 8 with the light path. A divider circuit 14 effects a division with the output from the second detector 13 as a denominator and the output from the first detector 12 as a numerator. An output from the divider is converted by a logarithmic amplifier 15 into a corresponding logarithmic value which is delivered out as a $CO_2$ concentration. A ray of light emitted from the light source 4 first falls on a lower one of the windows 3, then passes through a respiratory gas in the connector tube 2 and through the other window 3, and finally reaches the photodetector 10, as indicated by the arrowheads. When the motor 9 is energized, the chopper 6 which is interposed between the window 3 and the photodetector 10 is rotated to interrupt the light path periodically, thereby allowing light to be transmitted intermittently through the chopper 6. Therefore, the photodetector 10 converts the intermittent light into an electric signal.

The amplifier 11 amplifies the electrical signal output entering as an input from the photodetector 10.

The first detector 12 detects an output from the amplifier 11 in synchronism with passage of the light through the filter 7 and produces an output which corresponds to Vs in the equation (1). The second detector 13 detects an output from the amplifier 11 in synchronism with passage of the light through the filter 8 and produces an output Vc which is free of any influence of the $CO_2$ concentration, that is, corresponds to Vo in the equation (1). The output Vo tends to drift due to variations in the amount of light given off from the light source 4, variations in the sensitivity of the photodetector 10, and other factors. On the assumption that Vc=Vo, an output voltage $V_D$ from the divider circuit 14 is expressed by:

$$V_D = \frac{V_s}{V_c} = \frac{V_o e^{-KC}}{V_o} = e^{-KC} \qquad (2)$$

Thus, any influence of drifts can be compensated for. However, if temperature-dependent coefficients of detected outputs dependent on the light rays of the different wavelengths (absorbed wavelength and unabsorbed wavelength) are different from each other due to variations in the temperature of the light source or characteristics of the photodetector, then Vc≠Vo, resulting in drifts. The photodetector which uses e.g. PbSe in practice is still subjected to temperature-dependent drifts for the reason described above.

SUMMARY OF THE INVENTION

It is an object of the present invention to improve temperature-dependent characteristics of a respiratory gas concentration measuring apparatus of the type disclosed in Japanese Laid-Open Patent Publication No. Sho 57-23843.

The present invention is based on the findings that temperature-dependent drifts of the outputs from the detectors 12, 13 in the apparatus shown in FIG. 1 are combinations of temperature-dependent drifts of all components of the systems from the light source 4 and the photodetector 10 to the detectors 12, 13, particularly, the photodetector 10 (using PbSe, for instance), and that these temperature-dependent drifts are in exponential relation to temperature-dependent coefficients inherent in the wavelengths within a certain temperature range (from 10° C. to 40° C.). Assuming that a temperature-dependent coefficient with respect to the wavelength which is absorbed by $CO_2$ gas is $\theta_1$, and a temperature-dependent coefficient with respect to the wavelength which is not absorbed by $CO_2$ gas is $\theta_2$, the following equations are established:

$$V_s = S_{01} \exp(-\theta_1 T) \cdot \phi_{01} \cdot \exp(-KC) \qquad (3)$$

$$V_c = S_{02} \exp(-\theta_2 T) \cdot \phi_{02} \cdot \exp(-KC) \qquad (4)$$

where $S_{01}$: light sensitivity to the absorbed wavelength at 0° C., $S_{02}$: light sensitivity to the unabsorbed wavelength at 0° C., $\phi_{01}$: amount of incident light of the absorbed wavelength, and $\phi_{02}$: amount of incident light of the unabsorbed wavelength.

According to the present invention, based on the foregoing relationship between the outputs from the detectors, temperature compensation is effected by raising Vc in the equation (4) to the mth power, m being a temperature-dependent coefficient ratio $\theta_1/\theta_2$, and then dividing Vs in the equation (3) by the raised Vc. More specifically, $$\frac{V_s}{V_c^m} = \frac{S_{01} \cdot \phi_{01}}{S_{02}^m \cdot \phi_{02}^m} \cdot \frac{\exp(-\theta_1 T) \cdot \exp(-KC)}{\left\{\exp\left(-\frac{1}{m}\theta_1 T\right)\right\}^m} = \qquad (5)$$

$$\frac{S_{01} \cdot \phi_{01}}{S_{02}^m \cdot \phi_{02}^m} \cdot \exp(-KC)$$

Therefore, the term influenced by temperatures is eliminated.

The above and other objects, features and advantages of the present invention will become more apparent from the following description when taken in conjunction with the accompanying drawings in which a preferred embodiment of the present invention is shown by way of illustrative example. Identical reference numerals denote identical parts throughout the views.

DESCRIPTION OF THE PREFERRED EMBODIMENT

Figure 1:
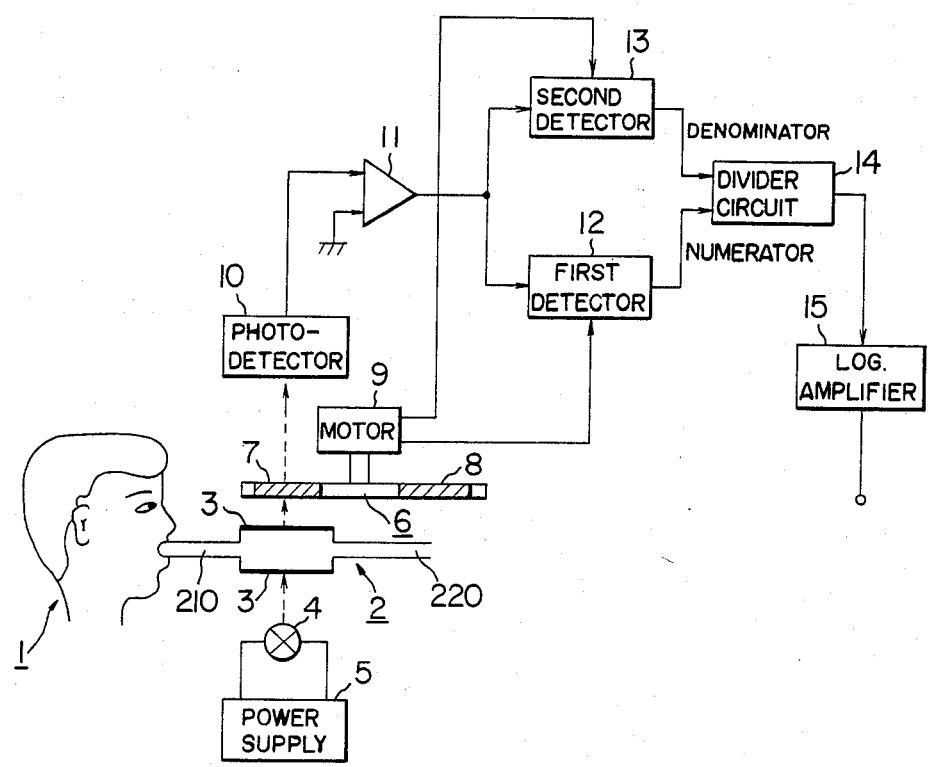
FIG. 1 is a schematic diagram, partly in block form, of a conventional respiratory gas concentration measuring apparatus.
Figure 2:
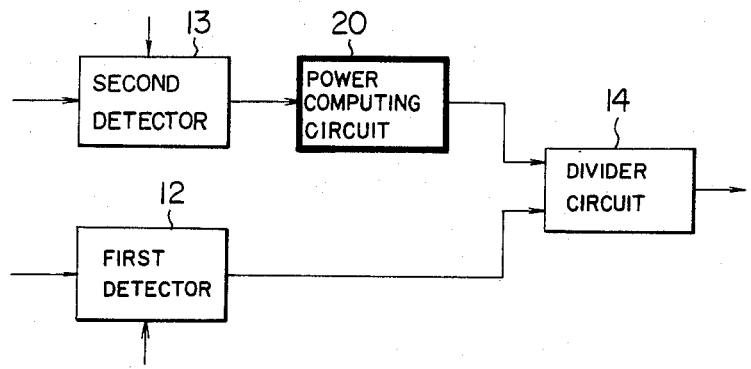
FIG. 2 is a block diagram of a portion of a respiratory gas concentration measuring apparatus according to the present invention.

An apparatus according to the present invention includes a power computing circuit 20 inserted between the second detector 13 and the divider circuit 14 in the apparatus of FIG. 1, as shown in FIG. 2. The power computing circuit 20 is composed, for example, of a power computing amplifier (for example, 443 manufactured by Analog Device Co.) for raising the output from the second detector 13 corresponding to Vc in the equation (2) to the mth power for thereby generating a signal indicative of $V_c^m$. The power exponent m is obtained by computing the ratio between temperature-dependent coefficients $\theta_1$, $\theta_2$ detected on the basis of temperature-dependent variations in the outputs from the detectors, or is rendered variable in the power computing circuit 20 and experimentally determined at an optimum level. It has been confirmed that the power exponent m is normally in the range of from 1.1 to 1.2 for $CO_2$ measurement. Since the wavelength of an infrared ray used varies with gas types to be measured, the power exponent m should be determined each time a different gas is to be measured.

For measuring a respiratory gas, for example $CO_2$, the first detector 12 produces an output voltage Vs given in the equation (3) dependent on the gas concentration as described with reference to FIG. 1. The output Vs drifts as an exponential function of the coefficient $\theta_1$, with respect to a temperature variation. The second detector 13 produces an output voltage which serves as a reference voltage irrespective of the gas concentration, that is, the output Vc referred to in the equation (4). The output Vc drifts as an exponential function of the coefficient $\theta_2$ with respect to a temperature variation. The output Vc is then raised to the mth power in the power computing circuit 20, which produces an output voltage corresponding to $V_c^m$. The divider circuit 14 effects a division as indicated by the equation (5) to generate an output $V_D$ corresponding to $$\frac{S_{01} \cdot \phi_{01}}{S_{02}^m \cdot \phi_{02}^m} \exp(-KC)$$

This output is linearized by the logarithmic amplifier 15, which produces an output voltage proportional to the $CO_2$ concentration C.

As long as the output voltages from the detectors vary exponentially with respect to a temperature variation, a gas concentration free of temperature-dependent drifts can be measured with high accuracy by presetting, as a power exponent in the power computing circuit, the ratio between temperature-dependent coefficients with respect to wavelengths that are absorbed and not absorbed by a gas to be measured.

Although a certain preferred embodiment has been shown and described, it should be understood that many changes and modifications may be made therein without departing from the scope of the appended claim.

What is claimed is:

1. A system for measuring the concentration of a respiratory gas that absorbs light having a first wavelength, including:
   (a) a connector tube having an open first end for receiving the respiratory gas, an opposite open end, and an air-tight window between ends;
   (b) a light source located adjacent a first side of the window for directing light through said window;
   (c) a chopper located adjacent a second side of the window in the path of the light directed through the window, including
      (1) at least one first filter means for passing through the light of a first wavelength from said light source, and
      (2) at least one second filter means for passing through the light from said light source of a wavelength that is not absorbed by said respiratory gas;
   (d) motor means connected to the chopper to position said first and second filter means alternately in said light path;
   (e) a photodetector means located adjacent the chopper for receiving light passing therethrough and converting the light having passed through said filter means into a first electric signal;
   (F) a first detector means connected to the photodetector means for receiving the first electric signal therefrom and operated synchronously with said motor means for generating a second electric signal indicative of the amount of light passing through the first filter means;
   (g) a second detector means connected to the photodetector means for receiving the first electric signal therefrom and operated synchronously with said motor means generating a third electric signal indicative of the amount of light passing through the second filter means; the improvement comprising:
   (h) a power computing circuit means connected to the second detector means for receiving the third electric signal therefrom and generating a fourth electric signal equal to the third electric signal raised to a preset mth power, m being the ratio between (1) a temperature-dependent coefficient $\theta_1$ of the second electric signal which varies exponentially with a temperature variation, and
(2) a temperature-dependent coefficient $\theta_2$ of the third electric signal which varies exponentially with a temperature variation; and
(i) a divider circuit means connected to the first detector means and the power computing circuit means for receiving the second and fourth electric signals and dividing the second electric signal by the fourth electric signal to produce a temperature independent electric signal indicative of the concentration of the respiratory gas in the connector tube.

\* \* \* \* \*

UNITED STATES PATENT AND TRADEMARK OFFICE
CERTIFICATE OF CORRECTION

PATENT NO. : 4,522,204
DATED : June 11, 1985
INVENTOR(S) : Kurahashi, et al.

It is certified that error appears in the above-identified patent and that said Letters Patent is hereby corrected as shown below:

Column 2, Equation (4), delete
"$Vc = S_{O2} \exp(-\theta_2 T) \cdot \phi_{O2} \cdot \exp -KC)$" and insert --$Vc = S_{O2} \exp(-\theta_2 T) \cdot \phi$--

Column 3, Line 42, delete "$V_c m$" and insert --"$V_c^m$"--

Column 3, Line 67, delete "$V_c m$" and insert --"$V_c^m$"--

Signed and Sealed this

First Day of October 1985

[SEAL]

Attest:

DONALD J. QUIGG

Attesting Officer

Commissioner of Patents and
Trademarks—Designate